United States Patent [19]

Dixon

[11] 4,124,371
[45] Nov. 7, 1978

[54] α,α-DIPHOSPHONATO ACETANILIDES

[75] Inventor: William D. Dixon, Kirkwood, Mo.

[73] Assignee: Monsanto Company, St. Louis, Mo.

[21] Appl. No.: 554,803

[22] Filed: Mar. 3, 1975

Related U.S. Application Data

[62] Division of Ser. No. 495,959, Aug. 9, 1974, Pat. No. 3,906,062.

[51] Int. Cl.$^2$ ............................................. A01N 9/36
[52] U.S. Cl. ............................................. 71/87; 71/86
[58] Field of Search ................................... 71/86, 87

[56] References Cited

U.S. PATENT DOCUMENTS

| | | | |
|---|---|---|---|
| 3,005,010 | 10/1961 | Grisley | 71/86 |
| 3,093,672 | 6/1963 | Miller | 71/86 |
| 3,455,675 | 7/1969 | Irani | 71/86 |

*Primary Examiner*—Catherine L. Mills
*Attorney, Agent, or Firm*—William I. Andress

[57] ABSTRACT

α,α-diphosphonato acetanilides are prepared by reacting a tetraalkylmethylenediphosphonate carbanion with an aromatic isocyanate or isothiocyanate. The said carbanion may be generated in situ by the reaction of an alkali metal or reactive compound thereof with a tetraalkylmethylenediphosphonate.

Compounds within the scope of the invention described herein are pesticidally active, e.g., as herbicides.

6 Claims, No Drawings

α,α-DIPHOSPHONATO ACETANILIDES

This is a division of application Ser. No. 495,959, filed Aug. 9, 1974.

BACKGROUND OF THE INVENTION

1. Field of the Invention

The invention herein pertains to the field of herbicides. In more particular, the invention pertains to the field of herbicides having as active ingredients compounds derived from the reaction of tetralkyl methylenephosphonate carbanion with aromatic isocyanates or isothiocyanates.

Description of the Prior Art

In the prior art are found various pesticidal, e.g., insecticidal or herbicidal compositions whose active ingredients are composed of compounds having various nitrogen/phosphorus/oxygen and/or sulfur-derived configurations, produced by a variety of methods. For example, in U.S. Pat. No. 3,057,774 are described insecticidal carbamoylalkyl phosphonothioate compositions prepared by the reaction of an ammonium or alkali metal salt of phosphonothioic acid with halohydrocarbylamide in an anhydrous medium.

A further example of prior art compounds as described above is found in U.S. Pat. No. 3,776,984 which discloses as pre-emergent herbicidal compounds S:dichloromethyl oxyphosphorus thioates prepared from substituted dichloromethane sulfenyl chlorides by reaction with a tertiary oxyphosphorus compound. Among various groups which may be substituted on the dichloromethane sulfenyl moiety are those having the —CONR$_2$ structure wherein the R's may be, e.g., hydrogen, phenyl or substituted phenyl.

Numerous other examples may be found in the prior art of pesticidal compounds having other nitrogen/phosphorus/oxygen and/or sulfur configurations. However, to applicant's knowledge, the compounds and process for preparing them as described herein are novel.

SUMMARY OF THE INVENTION

In one embodiment the present invention pertains to a novel class of α,α-diphosphonato acetanilides useful as herbicidal compounds. The compounds according to this invention have the following generic structural formula:

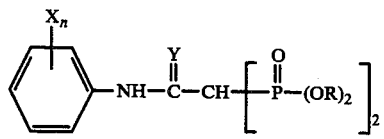

wherein X represents a hydrogen, halogen, CN, NO$_2$, NH$_2$ or a mineral acid salt thereof; $n$ is an integer from 0–5, preferably from 0–2; Y represents oxygen or sulfur and R is alkyl group having from 1–10 carbon atoms and preferably a lower alkyl group having from 1–5 carbon atoms.

In another embodiment of the invention herbicidal compositions are provided comprising said novel α,α-diphosphonato acetanilides as the active ingredient and an adduvant.

Still another embodiment of the invention consists of a novel process which comprises the reaction of a tetraalkylmethylenediphosphonate carbanion with an aromatic isocyanate or isothiocyanate. Suitably, said carbanion is generated in situ from the methylenediphosphonate by use of an alkali metal or alkoxide thereof. When X in the above generic formula is a nitro (NO$_2$) group, the reaction mixture may be treated with hydrogen to produce the corresponding amino (NH$_2$)-substituted compound; subsequent treatment with a mineral acid, e.g., a hydrohalide, produces a salt of said NH$_2$-substituted compound.

DESCRIPTION OF PREFERRED EMBODIMENTS

The process according to the present invention is believed to proceed according to the following typical reaction sequence (the X and R symbols are as defined above):

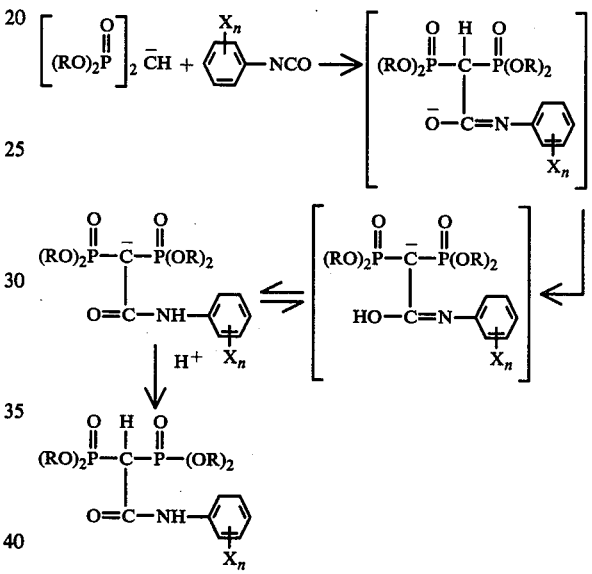

Analogous compounds wherein Y in the above generic formula is sulfur are produced when an isothiocyanate is substituted for the isocyanate in the above reaction sequence.

The invention will be more clearly understood by reference to the following detailed description of specific embodiments thereof.

EXAMPLE 1

This example describes the preparation of α,α-di(-diisopropylphosphonato)acetanilide.

Potassium metal, 2.0 g. (0.05 mol) cut into small pieces suspended in 200 ml of toluene and tetraisopropylmethylenediphosphonate, 17.2 g. (0.05 mol) was added over 30 minutes. When reaction of the metal was complete, phenyl isocyanate, 6.0 g. (0.05 mol), in 50 ml toluene was added and the reaction heated to 80° C. for 8 hours, at which time there was no isocyanate band in the infrared spectrum. The reaction mixture was cooled to room temperature and treated with 0.05 mol of glacial acetic acid and then 75 ml of water. The organic layer was separated, dried and solvent removed in vacuuo. The residue was subjected to chromatography on neutral alumina, eluding with benzene. Removal of solvent gave a residue which upon standing became a waxy solid.

Anal. Calc'd for $C_{20}H_{35}NO_7P_2$: C, 51.83; H, 7.61. Found: C, 52.29; H, 7.50.

EXAMPLE 2

In this example is described the preparation of α,α-di(diisopropylphosphonato)-4-chloroacetanilide. Potassium metal, 2.0 g. (0.05 mol), cut into small pieces suspended in 200 ml of toluene and tetraisopropylmethylenediphosphonate, 17.2 g. (0.05 mol), was added over 30 minutes. When reaction of the metal was complete, p-chlorophenyl isocyanate, 7.7 g (0.05 mol), in 50 ml toluene added. Reaction mixture was heated at 60° C. for 3 hours, cooled and treated with 3.0 g. (0.05 mol), glacial acetic acid and then 75 ml water. The organic layer was separated, dried over $MgSO_4$, filtered and evaporated. The residue was placed under petroleum ether and upon cooling 15.5 g. solid obtained, mp 114°–124° C. A small sample was recrystallized from petroleum ether, mp 128°–131° C.

Anal. Calc'd for $C_{20}H_{34}ClNO_7P_2$: C, 48.25; H, 6.88. Found: C, 48.50; H, 6.84.

EXAMPLE 3

This example describes the preparation of α,α-di-(diisopropylphosphonato)-4-nitroacetanilide.

Potassium metal, 2.0 g. (0.05 mol) cut into small pieces suspended in 200 ml of toluene and tetraisopropylmethylenediphosphonate, 17.2 g. (0.05 mol) added over 30 minutes. When reaction of the metal was complete, 4-nitrophenyl isocyanate, 8.2 g. (0.05 mol) in 100 ml of toluene added over 30 minutes. The reaction mixture was stirred four hours at 60° C., cooled and treated with 3.0 g of acetic acid and 75 ml of water. The organic layer separated, dried over $MgSO_4$, filtered and evaporated. Residue recrystallized twice from ethyl acetate, 5.1 g., mp 153°–157° C.

Anal. Calc'd for $C_{20}H_{34}N_2O_9P_2$: C, 47.25; H, 6.74. Found: C, 47.17; H, 6.88.

EXAMPLE 4

In this example, an aromatic isothiocyanate is used in place of an isocyanate to produce the corresponding thio compound.

Potassium metal, 2.0 g. (0.05 mol), cut into small pieces and suspended in 200 ml of toluene was warmed to 70° C. with stirring. Thereafter, the mixture was cooled to 30° C. and 17.2 g. (0.05 mol) of tetraisopropylmethylenediphosphonate was added dropwise and the mixture stirred until all the potassium had reacted, i.e., for about 2 hours. 8.0 g. (0.05 mol) of 4-cyanophenylisothiocyanate in 50 ml of toluene was then added dropwise and the mixture stirred for 2 days. The mixture was then treated sequentially with 5 ml of isopropanol 3 g. of acetic acid and 100 ml of water. The organic layer was separated, dried and condensed to an oil phase which solidified on cooling in dry ice; this solid had a melting point of 70°–82° C. After recrystallization from a carbon tetrachloride/petroleum ether mixture, 14.1 g. of product, α,α-di-(diisopropylphosphonato)-4-cyanoacetanilide, a yellow solid having a melting point of 85°–95° was recovered.

Anal. Calc'd for $C_{21}H_{34}N_2O_6P_2S$: C, 49.99; H, 6.79. Found: C, 50.99; H, 7.01.

EXAMPLE 5

This example illustrates a variation of the process of this invention using an alkali metal alkoxide compound in place of the alkali metal itself to generate the reactant carbanion.

To a mixture of 6.9 g. (0.062 mol) of potassium tert-butoxide in 75 ml of toluene was added 17.2 g. (0.05 mol) of tetraisopropylmethylenediphosphonate. This mixture was stirred for 2 hours, then 9.4 g. of 3,4-dichlorophenylisocyanate were added dropwise and stirred overnight. The mixture was then neutralized with 5.6 g. of glacial acetic acid. The organic layer was washed with water, dried and a yellow solid product condensed therefrom having a melting point of 96°–115° C. The product was recrystallized twice in heptane and dried in vacuuo to give 18.1 g. of a product identified as α,α-di-(diisopropylphosphonato)-3,4-dichloro-acetanilide, having a melting point of 122°–125½° C.

Anal. calc'd for: $C_{20}H_{33}Cl_2NO_7P_2$: C, 45.12; H, 6.79. Found: C, 44.67; H, 6.28.

EXAMPLE 6

The $NO_2$-substituted products of this invention, typified in Example 3, may be hydrogenated to produce the amino ($-NH_2$) analog thereof which, in turn, may be reacted with a mineral acid, e.g., the hydrohalides, HCl, HBr, HI or HF. to give the salt thereof as illustrated in this example. This example further illustrates the use of compounds of this invention as intermediates in the preparation of other compounds.

α,α-di-(diisopropylphosphonate)-4-nitroacetanilide, 2.0 g., dissolved in 50 ml ethanol and 0.01 g. platinum oxide catalyst added. The reaction mixture was subjected to hydrogenation at 50 p.s.i. for 4 hours. The catalyst was removed by filtration, the filtrate evaporated and the residue dissolved in ether. The ether solution was saturated with anhydrous hydrogen chloride and an oil separated. The oil titurated with acetonitrile to give a solid which was recrystallized by dissolving in a minimum of isopropanol followed by addition of ethyl acetate. The product, which does not have a distinct melting point, was recovered in an amount of 0.8 g. and identified as α,α-di-(diisopropylphosphonato)-4-aminoacetanilide hydrochloride.

Anal. Calc'd for $C_{20}H_{37}ClN_2O_7P_2$: C, 46.65; H, 7.24. Found: C, 46.77; H, 7.37.

The process variations according to the present invention have no critical parameters for the operation thereof. That is, temperatures and concentrations of reactants, time of reaction, etc., are straightforward and will be selected by those skilled in the art to accomplish the intended result within the scope of the exemplified invention having reference to the particular materials used and products obtained. Thus, the tetraalkylmethylenediphosphonate, alkali metal or reactive compound thereof and aromatic isocyanate or isothiocyanate may be reacted in such concentrations at such temperatures and times as effects formation of the invention compounds described herein. Temperatures suitable for reaction of the tetraalkyl methylenediphosphonate with the alkali metal or compound thereof to produce the phosphonate carbanion may be within the range of from about 20° C. to about 110° C., preferred operating temperature ranges are from about 30° C. to about 80° C. Reaction of the isocyanate or isothiocyanate reactant with said phosphonate carbanion may be performed in equimolar quantities, although more or less of either may be used, at temperatures within a range of from about 20° C. to 120° C., preferably from about 30° C. to about 60° C.

Further modifications within the process of this invention, as indicated above, include the use of reactive compounds of the alkali metals, such as the hydrides, alkoxides and alkyls of lithium, sodium, potassium, rubidium and cesium to generate the phosphonate carbanion. The alkoxide and alkyl moieties in these compounds may have generally from 1-10 carbon atoms and preferably from 1-5 carbon atoms. Obviously, other inert carriers, diluents or solvents may be used in which to conduct the above-exemplified reactions. For example, aliphatic and cycloaliphatic hydrocarbons such as the alkanes, alkenes, cycloalkanes and cycloalkenes customarily used for such purposes. Also suitable are aromatic hydrocarbons, such as the xylenes, etc., halogenated hydrocarbons such as the halobenzenes, etc. Heterocyclic compounds, e.g., tetrahydrofuran, etc., may also be used as a reaction medium herein.

Additional compounds produced according to the process of this invention include those wherein, referring to the generic formula above, X is a chloro, bromo, iodo or fluoro radical which may be substituted in from 0-5 positions on the anilide ring. Also, R in the above formula may be the same or different of any $C_{1-10}$ alkyl group, preferably a $C_{1-5}$ alkyl group, which may be straight or branched-chain.

Compounds according to this invention have been found to be herbicidally active when applied preemergently and/or post-emergently, as typified by the examples below.

EXAMPLE 7

Contact herbicidal activity of representative $\alpha,\alpha$-di-(dialkylphosphonato) acetanilides of this invention is determined by the following procedure:

The compound to be tested is applied in spray form to plants of a given age of several grasses and broadleaf species. After the plants are the desired age, each aluminum pan of plants is sprayed with a given volume of a 0.2% concentration solution of the candidate chemical, corresponding to a rate of approximately 4 lbs. per acre. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil-ethylene oxide condensate having about 6 moles of ethylene oxide per mole of tall oil. The injuries to the plants are then observed approximately 14 days later and the results are recorded.

Contact herbicidal activity of the compound prepared in Example 2 is observed against morningglory. Contact herbicidal activity of the compound prepared in Example 3 is observed against morningglory and lambsquarters. Contact herbicidal activity of the compound prepared in Example 4 is observed against cocklebur, quackgrass, Johnsongrass, lambsquarters and downy brome.

EXAMPLE 8

Pre-emergent herbicidal activity of representative $\alpha,\alpha$-di(dialkylphosphonato) acetanilides of this invention is determined by the following procedure:

A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

Pre-emergent activity of the compound prepared in Example 2 is observed against Canada thistle. Pre-emergent activity of the compound prepared in Example 1 is observed against lambsquarters and Johnsongrass. Pre-emergent activity of the compound prepared in Example 3 is observed against nutsedge.

The herbicidal compositions of this invention including concentrates which require dilution prior to application contain an effective amount of at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention can also contain other additaments, e.g., fertilizers, herbicides, other pesticides and the like used as adjuvants or in combination with the above-described adjuvants.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which residue in the present invention including all features which would be treated as equivalents thereof by those skilled in the art to which the invention pertains.

What is claimed is:

1. Herbicidal compositions comprising an adjuvant and an effective amount of a compound having the formula

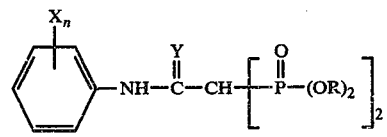

wherein:
X is halogen, CN, $NO_2$, $NH_2$ or mineral acid salt thereof;
n is an integer from 0–5;
Y is oxygen or sulfur and the
R's are alkyl groups having from 1–10 carbon atoms.

2. Composition according to claim 1 wherein in said formula n is zero.

3. Composition according to claim 1 wherein in said formula X is CN, n is 1 and each R is isopropyl.

4. Composition according to claim 3 wherein in said formula Y is sulfur.

5. Composition according to claim 1 wherein in said formula X is $NO_2$, n is 1 and each R is isopropyl.

6. Composition according to claim 1 wherein in said formula X is halogen, n is 1 and each R is isopropyl.

* * * * *